United States Patent [19]

Inouye et al.

[11] Patent Number: 4,595,549
[45] Date of Patent: Jun. 17, 1986

[54] CAPSULE AND CLAMPING APPARATUS FOR LOCATING AND EMBEDDING A SPECIMEN AND A METHOD FOR USING THE SAME

[75] Inventors: Tohru Inouye; Lai-Chun J. Tong, both Chicago, Ill.

[73] Assignee: Syprocode, Inc., Chicago, Ill.

[21] Appl. No.: 729,950

[22] Filed: May 2, 1985

[51] Int. Cl.⁴ .............................................. B29C 1/00
[52] U.S. Cl. ................................ 264/267; 264/279.1; 249/83; 249/121; 249/163; 249/167; 249/170
[58] Field of Search ...................... 425/117, 110, 318; 249/83, 117, 120, 121, 163, 167, 170; 264/267, 271.1, 279, 279.1

[56] References Cited

U.S. PATENT DOCUMENTS

| | | |
|---|---|---|
| 2,235,964 | 3/1941 | Meyer et al. ............ 249/83 X |
| 2,704,928 | 3/1955 | Curry ...................... 249/120 |
| 2,996,762 | 8/1961 | McCormick ............. 425/117 X |
| 3,014,614 | 12/1961 | Carroll et al. ........... 249/160 X |
| 3,104,665 | 9/1963 | Towns ...................... 249/120 X |
| 3,113,672 | 12/1963 | Brown ..................... 249/83 X |
| 3,565,389 | 2/1971 | Price ....................... 249/121 |
| 3,571,867 | 3/1971 | Cooke ..................... 249/83 X |
| 3,982,862 | 9/1976 | Pickett et al. ........... 249/83 X |

*Primary Examiner*—J. Howard Flint, Jr.
*Attorney, Agent, or Firm*—Gary, Juettner & Pyle

[57] ABSTRACT

An improved capsule and clamping apparatus and a method of using the same are disclosed. The capsule has a filling end and specimen end with a preformed opening at its filling end. The capsule has portions on the filling end for holding the capsule in a perpendicular position on a slide or the like so that the capsule may be clamped perpendicular in sealed relationship with the slide. Embedding material can then be poured into the filling end of the capsule for quickly preparing an accurate, embedded specimen block for later use, such as preparing sections, and particularly thick sections (1 to 6 microns) on a microtome machine, for microscopic examination.

28 Claims, 11 Drawing Figures

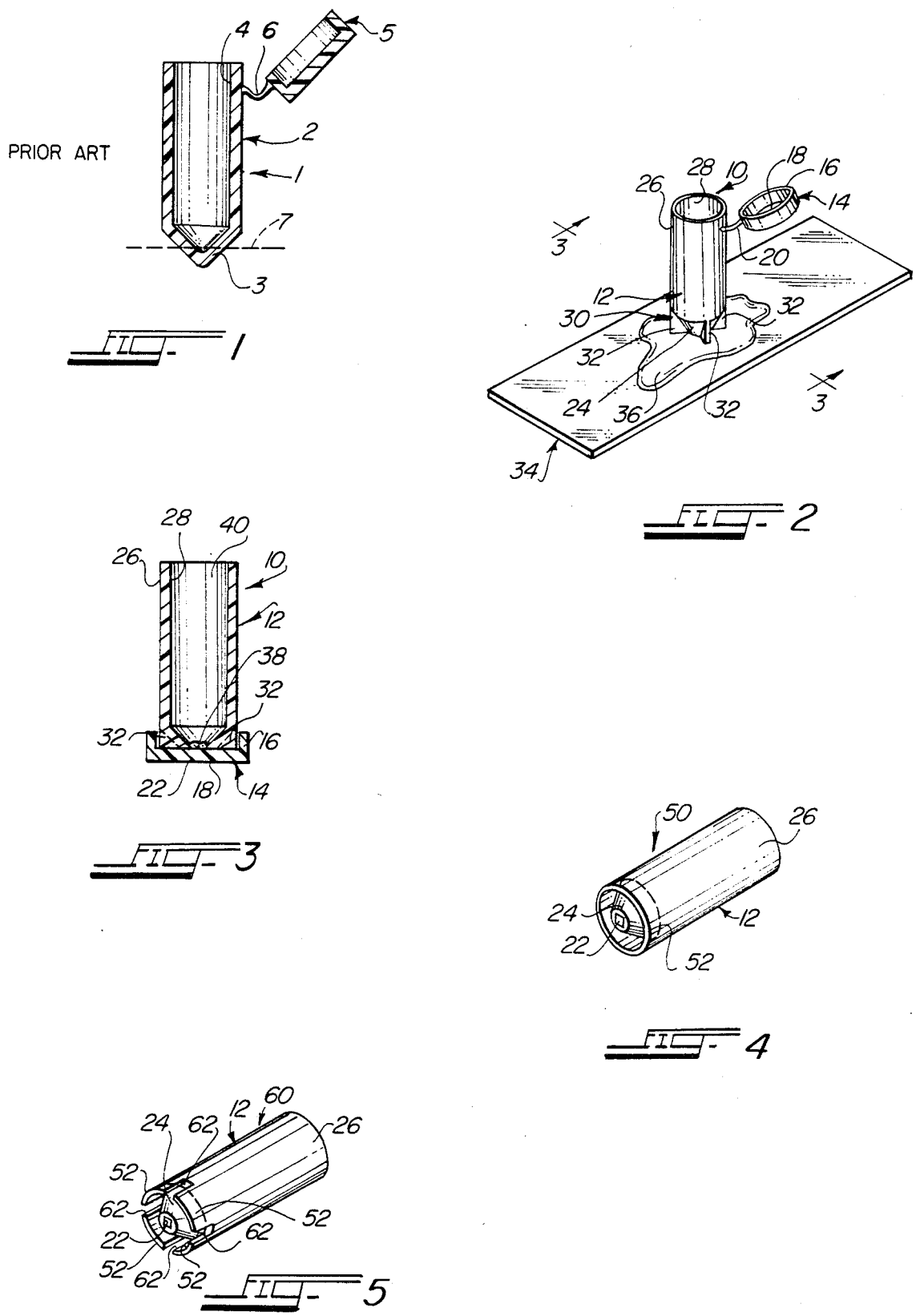

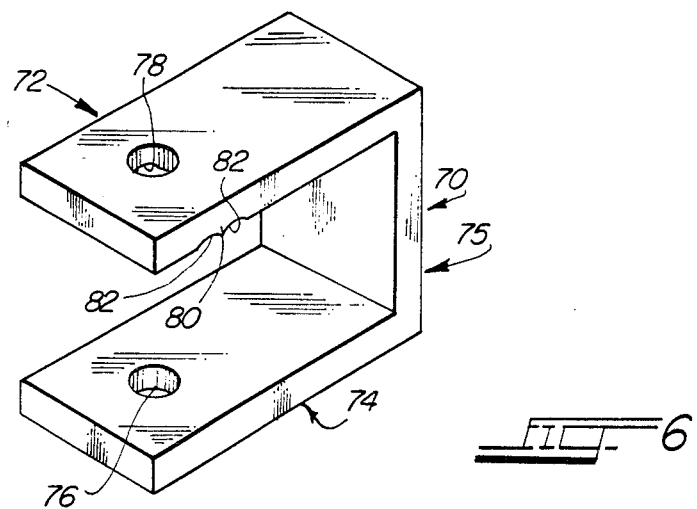
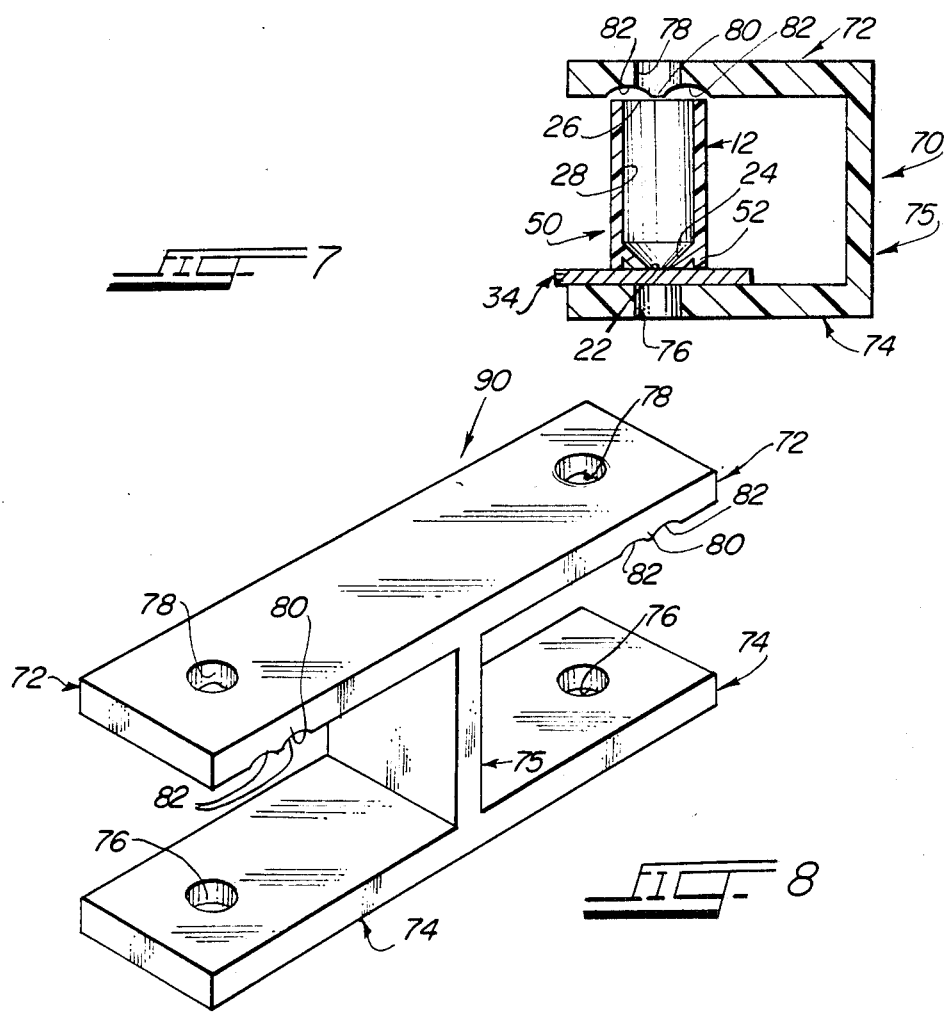

CAPSULE AND CLAMPING APPARATUS FOR LOCATING AND EMBEDDING A SPECIMEN AND A METHOD FOR USING THE SAME

This invention relates to an improved capsule and clamping means and a method for using the same for quickly and accurately preparing an embedded specimen for subsequent sectioning, and particularly for the preparation of such embedded specimen blocks for making thick sections (1 to 6 microns) on a microtome machine or the like, for further examination under an electron microscope.

This application also relates to a corresponding application Ser. No. 729,949, entitled "A Method And Apparatus For Locating And Embedding A Specimen", and filed on May 2, 1985. The cross-referenced application is particularly directed to an apparatus and method for preparing specimen blocks for making thin sections (0.10 to 0.08 microns).

BRIEF DESCRIPTION OF THE PRIOR ART

By way of background, usually when preparing for electron microscopic examination, a preliminary examination of a conventional slide specimen is first made with a lower power microscope to locate, for example, a particular tissue structure of interest, such as a cell. The desired structure may be visibly very small; for example, a cell may have a visible length and width on the order of 20 microns or less. In order to examine at high magnification, for example the cell's interior, what is done is first cut a thick section, 1 to 6 microns, off the original specimen to expose its structure. This thick section is then examined again at still higher power for the desired structure, and may eventually be reembedded and cut into thin sections (0.1 to 0.08 microns).

One method for preparing a thick sectioning specimen was to use a prior art embedding capsule. One source of prior art capsule was Better Equipment for Electron Microscopes, Inc. of Bronx, N.Y., which sold suitable capsules under the trademark BEEM. As illustrated in FIG. 1, this prior art capsule has a cylindrical body 2 with a closed specimen end 3, an open filling end 4 and a cap 5 for closing the filling end connected by a small tab 6. Such a capsule was used to form the specimen block which, in turn, was sectioned in a microtome machine, such as of the general type shown in U.S. Pat. No. 4,484,503 and/or U.S. Pat. No. 3,845,659 or sold under the trademarks and manufactured by the following:

SORVALL ULTRAMICROTOME
DuPont Instrument Products
Newton, Conn.,

REICHERT OmU2
C. Reichert Optische Werke, A.G.
Wien, Austria, and

ULTROTOME III
LKB 'Bromma, Sweden.

In order to prepare the specimen block from the prior art capsule various techniques were used. In the prior art technique shown in FIG. 1, the capsule's pointed or closed end was turned downwardly. Then the tissue to be embedded was simply dropped in the capsule, and the capsule filled with epoxy or other suitable embedding material. The resin eventually hardened to form the specimen block with the desired tissue structure specimen at its tip. The hardened block, after it was removed from the capsule with the specimen at its tip, was then mounted in the microtome machine for sectioning. Of course, with such technique the alignment of the tissue was totally random, and there was literally no way to insure the desired structure would appear at the face of the hardened resin block formed in the capsule, or oriented in the proper manner. With this approach it was only luck which would permit such a block to be usefully sectioned as there was no way no way to keep track of the location of the desired structure.

Another somewhat more efficient prior art technique used to form a specimen block, was to manually cut off a small part of the closed end (indicated by the dashed line 7) of the capsule with a razor to form an opening, and then try to manually locate this cut opened end over the desired tissue structure, usually located on a slide or the like. This approach had the advantage of at least to some degree better controlling the position of the desired structure. However, problems still arose as it was impossible to manually cut off the end of the capsule perfectly perpendicular to its axis. Some technicians tried to merely stand the capsule on its small cut off end, while others tried to hold the capsule in place manually while filling the capsule with an embedding material, such as a suitable epoxy resin. All too many times the resulting epoxy resin block containing the embedded specimen was inexact as the capsule had been held at a slight angle when initially positioned or the resin hardened. Thus, after the resin hardened, it was difficult to accurately and exactly cut the embedded tissue as it too was at an angle instead of being perpendicular to the relative path of the cutting edge of the blade of the microtome machine. If the capsule and resulting embedded, epoxy resin held, tissue specimen was off slightly from perpendicular, a few seconds of a degree, it made accurate sectioning of the specimen difficult. Generally, in order to make an accurate sectioning cut of say 1 to 6 microns thick from a tissue sample over a small surface (say 500–1000 microns wide and long), the path of the cutting edge of the microtome blade relative the specimen being sectioned had to be in angular alignment within a few seconds. That is, it is important to get the face of the resin block containing the specimen, to align parallel to the relative path of the cutting edge of the blade of the microtome machine. When the initial angular alignment of the tissue specimen in its resin block was more than a few seconds off perpendicular, it made it more difficult, if not impossible, and time consuming, to align the block and/or specimen in the microtome machine to the required accuracy.

Another prior art technique used to form the sectioning specimen was to invert the prior art capsule on the slide so that its big end was in contact with the desired portion of the slide specimen. While with this approach the broad end of the capsule was utilized to hold it, perhaps, closer to perpendicular, it had the disadvantage of making it difficult, if not impossible, to locate the desired tissue accurately in the center, and then required the technician, while at times looking through a microscope, to trim the big end of the capsule and hardened epoxy to near a point, all without cutting off the desired target area. Also, the last two prior art techniques had the disadvantage of the epoxy frequently leaking out of the capsule onto the slide/specimen.

When these prior art techniques were used, they required sometimes, many attempts and much time to arrive at usable sectioned specimens. No matter which prior art technique was used, all too frequently because the desired tissue was not knowingly or properly located, or located at even a small angle, the cut section was not correct or exact enough for further study. For example, the microtome cut would not be deep enough leaving the tissue's structure unexposed, or too deep so that the desired tissue structure was cut away and/or destroyed. The inaccuracies of the prior art capsule and techniques made it extremely difficult for even a well trained, experienced technician to quickly and efficiently prepare embedded specimen blocks.

BRIEF DESCRIPTION OF THE INVENTION

The present invention provides an improved capsule and clamping apparatus and a method of using the same by which, after a little training and experience, a technician can quickly prepare a sectioning specimen block for microscopic examination, generally on the first try, and is particularly useful for preparing specimen blocks for thick sections of 1 to 6 microns thick.

The apparatus comprises a special capsule having an already formed or preformed opening at its specimen end which is on the axis of the capsule and perpendicular thereto. Further, the margins of the opening are capable of sealing with the slide. In addition, the capsule has means on its specimen end for holding the capsule perpendicular on a slide such as a conventional microscopic slide or other suitable flat, glass, plastic, etc. surface or the like. This special capsule is used in conjunction with a special capsule clamping means for clamping the capsule's preformed opening to the slide and holding the capsule perpendicularly in place on the slide so that target area containing the desired tissue structure may be embedded (or even reembedded). The method of the present invention comprises the steps of accurately locating the capsule with a preformed opening over the subject tissue, which is positioned on a slide or the like, clamping the capsule, which is to contain the embedding epoxy resin, or other suitable material forming the specimen block, generally perpendicular to the slide, then filling the capsule with epoxy resin, or other suitable material, and permitting the same to harden while the capsule is still clamped in the perpendicular position.

By using the apparatus and the method of the present invention, specimen blocks are quickly and easily prepared. The improved capsule of the present invention can be accurately located exactly over the desired target tissue or area, and the latter can be embedded very close to, if not exactly, perpendicular to the axis of the capsule. Thus, it then becomes relatively easy for a trained technician to make any minor adjustments in alignment when the completed specimen block is mounted on the microtome machine, estimate the desired depth of cut to make with the microtome machine (such as one of the machines mentioned above), and section through the tissue at the desired location.

A primary object of the apparatus and method of the present invention to permit a technician to quickly prepare specimen blocks for processing, such as making thick sectioning cuts (6 to 1 microns) on a microtome machine.

Another object of the apparatus and method of the present invention is to provide means for clamping an embedding capsule to a specimen slide or the like.

A further object of the apparatus and method of the present invention is to provide a preformed, accurate opening in the embedding capsule which has margins which can be sealed to the slide or the like.

Still another object of the present invention is to provide an embedding capsule with means thereon for holding the capsule perpendicular to the slide or the like and in sealed relationship therewith by a simple clamp.

These and other objects of the present invention will become apparent from the following written description and the accompanying figures of the drawings.

BRIEF DESCRIPTION OF THE FIGURES OF THE DRAWINGS

FIG. 1 is a cross-sectional view of a prior art capsule.

FIG. 2 is a perspective view of the one embodiment of an improved capsule of the present invention shown standing on a slide carrying a tissue specimen.

FIG. 3 is an enlarged cross-sectional view taken on the lines 3—3 of FIG. 2, but with the capsule's cap placed beneath it.

FIG. 4 is a perspective view of a second embodiment of an improved capsule of the present invention.

FIG. 5 is a perspective view of a third embodiment of an improved capsule of the present invention.

FIG. 6 is a perspective view of one embodiment of clamping means for use with the improved capsule of the present invention.

FIG. 7 is a cross-sectional view showing the improved capsule of FIG. 4 shown clamped to a slide or the like with the clamp shown in FIG. 6.

FIG. 8 is a perspective view of a second embodiment clamp in the form of a double clamp.

BRIEF DESCRIPTION OF THE PREFERRED EMBODIMENT

Figure 9:
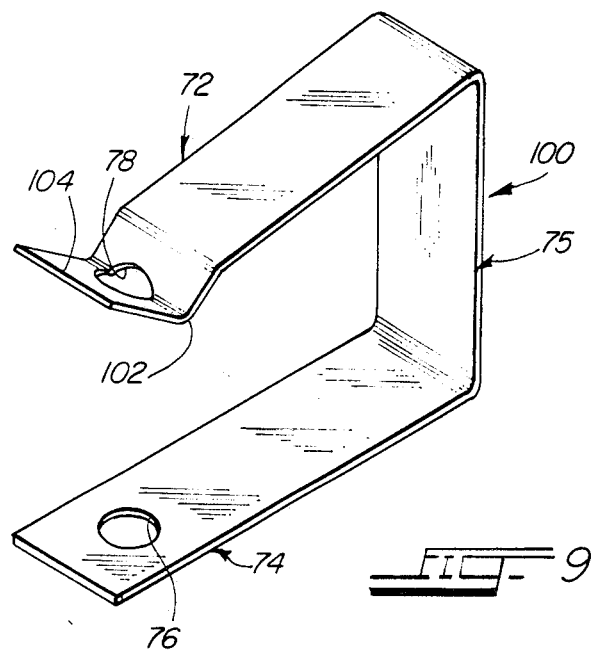
FIG. 9 is a perspective view of a third embodiment of a clamp made of flexible sheet metal.

The prior art capsule 1 has been briefly previously described and is shown in FIG. 1. An embodiment of improved capsule 10 of the present invention is shown in FIG. 2. The capsule 10 has a cylindrical body 12 of generally the same diameter, wall thickness and height as the prior art capsule. For many purposes the improved capsule 10 may be used interchangeably with the prior art capsule 1, and any existing equipment which will accommodate the prior art capsule 1 will be useable with capsule 10. Like the prior art capsule 1, the improved capsule 10 may have a cap 14, having a short, cylindrical side wall 16 and a flat, closing wall 18, and can be attached to the body of the capsule by a breakable tab 20. The capsule 10, its cap 14 and tab 20 can all be integrally molded together, and as will be described the tab 20 can be cut or otherwise broken to separate the cap 14 from the rest of the capsule.

Unlike the prior art capsule 1, the capsule 10 is provided with a preformed opening 22 (FIG. 3) at its tapered specimen end 24 for the tissue specimen to be embedded. The other or filling end 26 has a large opening 28 into which the embedding material, such as epoxy, can be droppered or poured. As is shown in FIG.

2, the capsule 10 has means 30 at its specimen end 24 for holding the capsule perpendicular or upright. In capsule 10, means 30 is in the form of a plurality of fins 32, in this instance four, integrally formed with the capsule's body. The fins 32 do not extend radially outward beyond the body so that the capsule 10 may be used interchangeable with the prior art capsule 1, such as with the apparatus of the above mentioned application, Ser. No. 729,949. The fins 32 also do not extend axially downwardly beyond the margins of the preformed specimen opening 22 so that the margins of that opening 22 can contact and seal with any generally flat member, such as a specimen carrying slide, placed below. For example, as shown in FIG. 2, the capsule 10 is held upright by its fins 32 on and generally perpendicular to the slide or the like 34 on which a tissue specimen 36 is located, and from which the small specimen (desired target area) to be embedded is to be taken.

Referring to FIG. 3, the versatility of the capsule of the present invention is illustrated. For example, capsule 10 can have its cap 14 detached and slipped into place beneath the fins 32 to close off the preformed opening 22. To provide sufficient support for the cap 14, it is best if three or more points of contact be provided on the perimeter of the capsule, such as by three or more fins 32. As is illustrated with the preferred opening 22 closed by the cap 14, a specimen to be embedded 38 may be dropped through the capsule's filling end 26, and settles at the specimen end 24. The capsule 10 can be then filled with epoxy or other suitable material 40 to form a specimen block when the material hardens. This block can then be removed from the capsule and further processed, such as sectioned. Thus, though the capsule 10 has a preformed opening 22 in it, it can also function like a prior art capsule 1 which is left uncut, without the need for any special equipment other than its own cap 14.

Referring to FIG. 4, a second embodiment capsule 50 is shown. The capsule 50 is generally similar to capsule 10, and similar features are given like reference numerals. The principal difference between capsule 50 and capsule 10 is that the lower end of cylindrical body of the capsule 50 is extended downwardly, as indicated at 52, generally to the plane of the lower margins of opening 22. This extension 52 of the body holds the capsule upright, instead of a plurality of fins 32 as used in capsule 10. For simplicity the cap of capsule 50 or subsequent capsules have not been shown.

Referring to FIG. 5, a third embodiment capsule 60 is shown. The capsule 60 is generally similar to capsule 50, and similar features are given like reference numerals. The principal difference between capsule 60 and capsule 50 is that the lower extended portion of the cylindrical body is broken or interrupted at several places, as indicated by the reference numeral 62, to give some flexibility to this outer lower wall to insure that the margins of the opening 22 will contact the slide, as will be hereinafter explained.

Referring now to FIG. 6, a first embodiment of clamp 70 of the present invention is shown, and is in this instance made of a flexible material such as plastic. The clamp 70 has three portions, an upper or capsule engaging portion 72, a lower or slide engaging portion 74, and a center or connecting portion 75. Each portion is of a width somewhat greater than the diameter or width of one of the capsules 10, 50 or 60, and the interior dimension between the upper and lower portions 72, 74 is about that of the height of a capsule 10, 50 or 60 plus the thickness of a slide or the like. The portions 72, 74 and 75 of the clamp are flexible and can be displaced slightly to permit a capsule 10, 50 or 60 and slide or the like to be installed, but then return and bias the portion 72 toward portion 74 to act as a clamp. The lower portion 74 has a viewing opening 76 to help align the slide specimen with the preformed opening 22 in the capsule. The upper portion 72 also has a filling opening 78 therein through which the embedding material may be added. In order to assure that the capsule is held close to vertical and not off center, line of contact means are provided on the underside of the upper portion 72. In this instance, the line of contact means is in the form of a ridge 80 formed by cutting two grooves 82 into the underside of the upper portion.

Referring now to FIG. 7, it can be seen how the capsule and clamp of the present invention interact. Any one of the improved capsules could be selected, but in this instance, capsule 50 has been illustrated. The preformed opening 22 in the capsule 50 is aligned over the desired target area on the specimen located on the slide 34. Then the capsule 50 and slide 34 are placed between the upper and lower portions 72 and 74 of the clamp 70. The slide is automatically held parallel to the lower portion 74 of the clamp, while the line of contact ridge 80 engages the upper edge of the cylindrical wall of the body 12 at two points. The lower extension of the cylindrical wall, indicated at 52, is pressed against the slide to hold the capsule upright and perpendicular. At the same time, the margins of opening 22 are pressed against the slide to seal therewith. If need be, the alignment of the capsule 50, its opening 22 and the target area on the slide can be checked by viewing through a microscope through opening 78. When the technician is satisfied with the alignment, the epoxy material can be poured or eye dropped through opening 78 to fill the capsule. After the embedding material hardens, the capsule may be removed from the clamp, and the capsule stripped from the hardened specimen block. As is conventional, the epoxy will penetrate the specimen, and when the slide 34 is removed, leave the specimen embedded in the tip of the hardened block.

Referring now to FIG. 8, a second embodiment 90 of clamping means is shown. Clamp 90 is actually a double clamp version of clamp 70, and like parts carry the same reference numerals. The principal difference between clamp 70 and clamp 90 is that in the latter there are two sets of integral joined upper portions 72 and lower portions 74 extending from a single center section 75. Clamp 90 has the advantage of being able to open one end of the clamp by squeezing the other end.

Referring now to FIG. 9, a third form of clamp 100 is shown and is made of a bent sheet material, such as stainless steel or brass. The parts of clamp 100 which are similar to those of clamp 70 are given similar reference numerals. The principal difference of the clamp 100 is that the line of contact portion is formed by a bend 102. At the same time the portion 72 is bent to extend upward to form a tip 104 to assist in releasing the clamp from a capsule.

Figure 10:
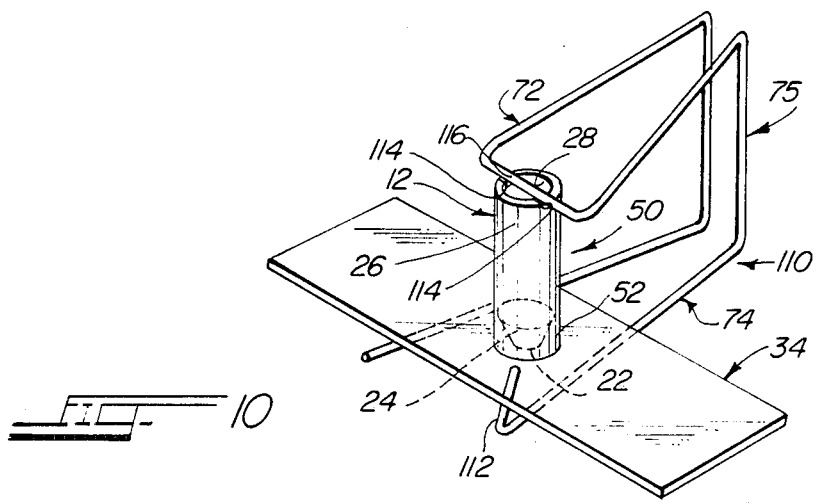
FIG. 10 is a perspective view of a fourth embodiment of a clamp made of wire showing an improved capsule, somewhat similar to that shown in FIG. 4, clamped to a slide.

Referring to FIG. 10, a fourth embodiment of clamp 110 is shown and is made of bent wire, such as brass, or steel. In this instance, the lower portion 74 is formed by the two ends of the wire, with one end 112 being bent back to provide a pointer to indicate where the slide, its specimen, the lower end of the capsule 50 and its opening 22, should be placed. The upper portion 72 and portion 75 are formed by the intermediate portions of the wire. As shown in this instance, the capsule 50 has been provided with means in the form of two notches 114 in the capsule body wall for receiving that part of the clamp and/or wire forming the line of contact 116. In this instance no viewing or filling opening need be provided as the slide, specimen and preformed opening 22 would be clearly visible around the wire, and the embedding material likewise can be poured around the wire.

Figure 11:
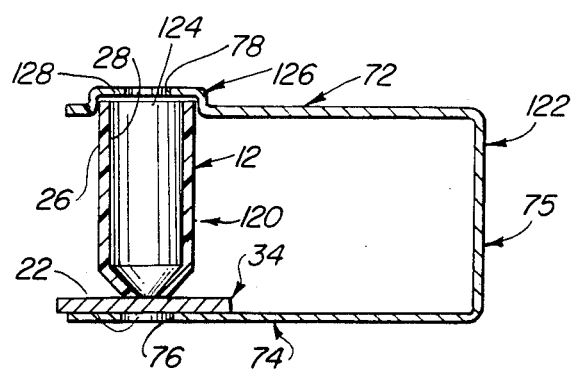
FIG. 11 is a cross-sectional view of a fifth embodiment of clamp and a fourth embodiment of capsule of the present invention.

Referring to FIG. 11, a fourth embodiment of capsule 120 and fifth embodiment of clamp 122 of the present invention are shown. Capsule 120 is generally similar to capsules 10, 50 or 60, and like parts carry the same reference numerals. The principal difference is that the capsule 120 is held perpendicular by the clamp 122 causing the margins of the preformed opening 22 to engage with the slide, and the clamp itself engaging with the upper rim 124 of the filling end 26. Clamp 122 is generally similar to clamps 70, 90, 100 or 110, and like parts carry the same reference numerals. The principal difference is that the clamp 122 has means 126, in this instance in the form of a female or recessed rim 128 on the upper portion 72 of the clamp, to locate the capsule perpendicularly relative to the slide. While the recessed rim 128, in this instance, has been formed in the metal of the clamp by simply displacing it, as by stamping, the recess could have also been formed by other means or in a plastic type clamp. Further, while the means 126 has been shown as a female recess for receiving the filling end 26 of the capsule 120, it could have just as well be formed by a male protrusion which fits within the opening 28 of the capsule 120, or by a combination of female recess and male protrusion. While clamp 122 is shown with capsule 120, it could also be made to work with any of the other capsules.

Thus, an improved capsule, such as any one of those previously described 10, 50, 60 or 120 can be stood perpendicularly on a slide or the like over the desired target area to be embedded. Then the clamp means, such as any one previously described 70, 90, 100, 110 or 122 can be placed under the bottom side of the slide or the like, and over the top of the capsule to clamp the capsule in place perpendicularly with its preformed opening sealed against the slide and/or specimen. The viewing opening in the lower portion and the filling opening in the upper portion, if provided, can be aligned with the specimen end and filling end of the capsule, respectively. The embedding material can then be placed in the capsule and permitted to harden while the capsule is still perpendicularly clamped in place. After the material has hardened the clamp can be removed, and the hardened specimen block, with the specimen at its tapered tip can be removed from the capsule. The resulting specimen block can then be placed in a microtome machine and easily and quickly sectioned, particularly into thick sections, 1 to 6 microns thick, as the specimens on the block is very close to perpendicular and in the same and known alignment as it was on the slide. Much if not all of the guess work and labor of the prior art techniques having been eliminated. With a little experience a technician can quickly form a good specimen block and cut good sections usually on the first try, with much less effort than was needed with the prior art capsule. Yet the capsule of the present invention when used with its accompanying cap retains the versatility of being used in the manner as shown in FIG. 3 to have a tissue specimen merely dropped in, all without the need for special stands. Further, the capsule of the present invention can also be used with the precision apparatus described in the above mentioned application Ser. No. 729,949, for making very accurate specimen blocks for cutting thin sections (0.1 to 0.08 micron thick).

While the capsule and clamp of the present invention means could also be used to make thin sections, and would be superior to prior art techniques to do so, it would not be as accurate and quick as using the precision apparatus and method shown in application Ser. No. 729,949, because the control and the degree of perpendicularity obtained by use of the simple clamp of the present invention is not as great as using the precision apparatus and method shown in application Serial No. 729,949.

While the present invention was described in connection with a tissue specimen, it should be understood that the apparatus and method could also be used with other specimens, such as ones prepared from tissue cultures or any specimens, biological or otherwise, that needs to be viewed or studied in sections. As used herein the specimens on the slide or the like are defined to include all such specimens. Also, while the apparatus and method of the present invention were described with cylindrical type capsules and blocks, it should be understood that the apparatus and method could be utilized with other size or type capsules and blocks for making embedded specimens. For example, the capsules and blocks could be rectangular, or just tips to be secured to other elements, the resulting blocks then being secured in the collet, chuck or vise of the microtome.

While several embodiments of the apparatus and methods of the present invention have been illustrated and described, from the foregoing, it should be understood that other variations, modifications, and equivalent structures and steps thereof fall within the scope of the appended claims.

What is claimed is:

1. An improved embedding apparatus for embedding a specimen or the like from a microscope slide or the like into a block, comprising a capsule having a generally hollow elongated body with a longitudinal axis adopted to be aligned with the axis of the microtome machine, said capsule having a filling end and a specimen end, a preformed opening in said capsule at said specimen end, said preformed opening being adapted to be placed over a target specimen area on the slide or the like, said preformed opening having margins for sealing around the target area, means on said capsule for holding said capsule perpendicular to the slide or the like, and means for clamping said capsule perpendicular to the slide or the like with said margins on said specimen end in sealing contact with the slide or the like, said filling end of said capsule being adapted to receive embedding material or the like for embedding the specimen; whereby said preformed opening may be located over the desired target specimen, said capsule then being clamped in place perpendicular to the slide or the like, and embedding material poured into said capsule to form an embedded specimen block.

2. An improved embedding apparatus as in claim 1, wherein said means for holding said capsule perpendicular extends from a point between said filling and specimen ends to said specimen end.

3. An improved embedding apparatus as in claim 2, wherein said means for holding said capsule perpendicular is in the form of three or more fins.

4. An improved embemdding apparatus as in claim 2, wherein said means for holding said capsule perpendicular is in the form of a downward extension of said hollow body.

5. An improved embedding apparatus as in claim 4, wherein said extension of said hollow body is interrupted in one or more places to provide flexibility to said extension to insure sealing of said margins with the slide or the like.

6. An improved embedding apparatus as in claim 2, wherein said means for holding said capsule perpendicular is integrally formed with said hollow body.

7. An improved embedding apparatus as in claim 1 further comprising a cap, said cap being engageable with said means for holding said capsule perpendicular and with said margins of said preformed opening to seal said preformed opening.

8. An improved embedding apparatus as in claim 1, wherein said means for clamping said capsule comprises a clamp having one or more portions for clamping said capsule to the slide or the like.

9. An improved embedding apparatus as in claim 8, wherein said capsule further comprises a clamp engaging portion adjacent to said filling end, said clamp means engaging said clamp engaging portion and the undersurface of the slide opposite the specimen.

10. An improved embedding apparatus as in claim 8, wherein said clamp means is in the form of an elongated element having a capsule engaging end, a slide engaging end and an intermediate connecting portion, said capsule engaging and slide engaging ends being biased relatively toward each other.

11. An improved embedding apparatus as in claim 10, wherein said clamp means is formed from bent wire.

12. An improved embedding apparatus as in claim 10, wherein said clamp means is formed from a bent, flexible elongated strip.

13. An improved embedding apparatus as in claim 10, wherein said clamp means is formed from flexible plastic material.

14. An improved embedding apparatus as in claim 10, wherein said capsule engaging end of said clamp means engages said filing end of said capsule in a line of contact.

15. An improved embedding apparatus as in claim 14, wherein said clamp means has an integral ridge for forming said line of contact for engaging said capsule.

16. An improved embedding apparatus as in claim 14, wherein said clamp means is bent to form said line of contact for engaging said capsule.

17. An improved embedding apparatus is in claim 10, wherein said clamp means has a filling opening therein adjacent said capsule engaging end to permit filling said capsule with embedding material.

18. An improved embedding apparatus as in claim 10, wherein said clamp means has a viewing opening therein adjacent said slide engaging end to assist in aligning the target specimen with said preformed opening in said capsule.

19. An improved embedding apparatus as in claim 18, wherein said clamp means.has a filling opening therein adjacent said capsule engaging end to permit filling said capsule with embedding material.

20. An improved embedding apparatus as in claim 14, wherein said capsule adjacent said filling end has cooperating means for providing said line of contact with said clamp means.

21. An improved embedding apparatus as in claim 20, wherein said cooperating means comprises one or more notches formed in said hollow body of said capsule.

22. An improved embedding apparatus as in claim 1, wherein said means for holding said capsule perpendicular comprises the margins of said preformed opening and a rim of said filling end, said clamp having means for engaging with said filling end.

23. An improved embedding apparatus as in claim 22, wherein said means for engaging said filling end comprises a female recess receiving said filling end of said capsule.

24. An improved embedding apparatus as in claim 23, wherein said means for engaging said filling end further comprises a male protrusion extending into said filling end of said capsule.

25. An improved embedding apparatus as in claim 24, wherein said means for engaging said filling end comprises a male protrusion extending into said filling end of said capsule.

26. An improved embedding apparatus as in claim 22, wherein said means for engaging said filling end of said clamp has a filling opening therein, whereby embedding material can placed into said capsule while said capsule is clamped perpendicular.

27. An improved embedding apparatus as in claim 1, further comprising a cap for closing said filling end, said cap fitting over said specimen end of said body and closing off said preformed opening, whereby said capsule can be used by merely dropping a specimen thereinto said specimen end of said capsule.

28. A method for forming an embedded specimen block from a slide mounted specimen or the like, using a capsule having specimen and filling ends, with a preformed opening in the capsule at its specimen end, comprising the steps of:

A. locating the preformed opening over and in contact with the desired target portion of specimen and the capsule perpendicular to the slide, B. clamping the filling end of the capsule and the underside of the slide towards each other with the preformed opening in sealed relationship with the slide, and C. pouring embedding material into the capsule and permitting the material to harden while the capsule is still clamped perpendicular to the slide, whereby an accurate block may be formed.

* * * * *